United States Patent [19]

Fujiki et al.

[11] Patent Number: 5,072,012

[45] Date of Patent: Dec. 10, 1991

[54] NOVEL ALKOXYSILANES

[75] Inventors: Hironao Fujiki; Toshiaki Takahashi, both of Annaka, Japan

[73] Assignee: Shin-Etsu Chemical Co., Ltd., Tokyo, Japan

[21] Appl. No.: 708,581

[22] Filed: May 31, 1991

[30] Foreign Application Priority Data

Jun. 1, 1990 [JP] Japan ................... 2-144024

[51] Int. Cl.$^5$ ............................................. C07F 7/18
[52] U.S. Cl. ............................................. 556/435
[58] Field of Search ...................................... 556/435

[56] References Cited

U.S. PATENT DOCUMENTS 3,109,826 11/1963 Smith ............................. 556/435 X
4,539,417 9/1985 Takamiezawa et al. ............. 556/435
4,788,311 11/1988 Inoue et al. ....................... 556/435
4,801,725 1/1989 Arai et al. ........................ 556/435 X

*Primary Examiner*—Paul F. Shaver
*Attorney, Agent, or Firm*—Millen, White & Zelano

[57] ABSTRACT

Novel alkoxysilanes of the general formula:

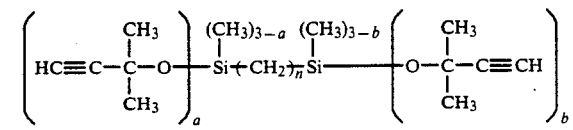

wherein letter a is equal to 2 or 3, b is equal to 0, 1, 2 or 3, and n is an integer of from 2 to 10 are useful agents for controlling curing reaction of addition type curable silicone compositions.

3 Claims, No Drawings

NOVEL ALKOXYSILANES

This invention relates to novel alkoxysilanes useful for controlling curing reaction of addition type curable silicone compositions.

BACKGROUND OF THE INVENTION

Prior art well-known agents for controlling curing reaction of addition type curable silicone compositions include acetylene alcohols, alkoxysilanes and alkoxysiloxanes derived from acetylene alcohols, and low molecular weight organovinylsiloxanes. These compounds, however, are not fully satisfactory curing control agents. There is a need for a compound which is more effective as a curing control agent.

SUMMARY OF THE INVENTION

Making investigations in search of useful agents for controlling curing reaction of addition type curable silicone compositions, the inventors have found that novel alkoxysilanes of the general formula:

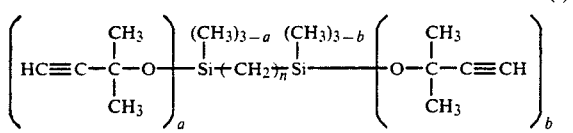

wherein letter a is equal to 2 or 3, b is equal to 0, 1, 2 or 3, and n is an integer of from 2 to 10 are obtained, for example, by effecting hydrosilylation between a chlorohydrogensilane and a vinylchlorosilane and effecting dehydrochlorination between the resulting 1,2-bis(chlorosilyl)ethane and 1,1-dimethylpropargyl alcohol. These alkoxysilanes are useful control agents for curing reaction of addition type curable silicone compositions.

The alkoxysilanes of formula (I) can be prepared from two types of readily available monosilane reactants by a relatively simple synthesis process and purified by distillation. Then when added to addition type curable silicone compositions as a curing reaction control agent, a certain amount of the alkoxysilane provides curing reaction control to a constant extent independent of its particular manufacturing lot. Curing of silicone compositions can be precisely controlled in a reproducible manner.

In addition, the alkoxysilanes defined herein have an extremely low vapor pressure at room temperature so that curable silicone compositions containing the alkoxy silane control agent may have a satisfactory life time and little alter their curing behavior when the compositions are subjected to vacuum debubbling prior to their use. When the compositions are heat cured at temperatures between 150° C. and 180° C., cured products are free from the risk of differential curing between the surface and the interior which would otherwise impair the outer appearance.

Although Japanese Patent Application Kokai No. 11160/1989 and Japanese Patent Publication No. 2627/1989 disclose α-ethynylalkoxysilanes having a hydrogen atom or a substituted or unsubstituted alkyl or aryl group attached to a silicon atom, the alkoxysilanes of formula (I) characterized by the attachment of an α-ethynylalkoxy group to a silicon atom of silethylene are novel compounds that the inventors have discovered.

DESCRIPTION OF THE PREFERRED EMBODIMENTS

The present invention provides alkoxysilanes of formula (I).

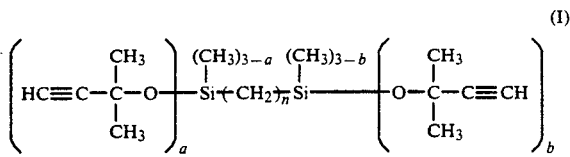

In formula (I), letter a is equal to 2 or 3, b is equal to 0, 1, 2 or 3, and n is an integer of from 2 to 10. Exemplary are α-ethynylalkoxysilanes of the following formulae.

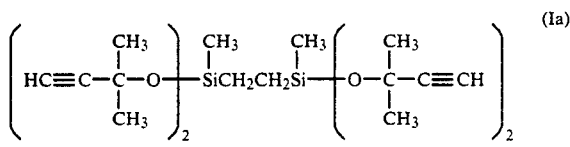

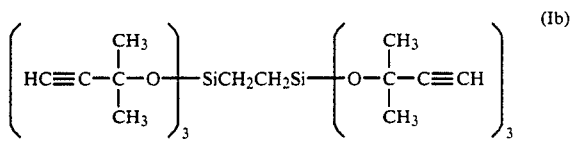

The alkoxysilanes of formula (I) according to the invention are obtained simply by effecting hydrosilylation between a chlorohydrogensilane having a hydrogen atom attached to the silicon atom and an alkenylchlorosilane having a C$_{2-10}$ alkenyl group attached to the silicon atom such as vinyl and allyl to form a bis(chlorosilyl)ethane, and subjecting the bis(chlorosilyl)ethane to dehydrochlorination using 1,1-dimethylpropargyl alcohol. For example, the α-ethynylalkoxysilanes of formulae (Ia) and (Ib) illustrated above may be synthesized according to the following reaction scheme.

Scheme A

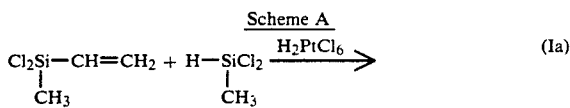

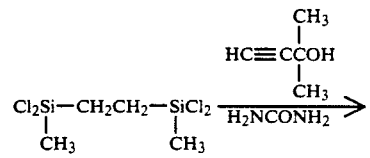

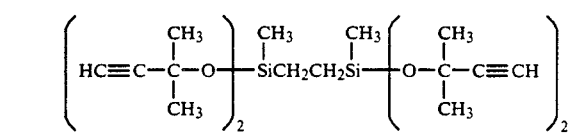

Scheme B

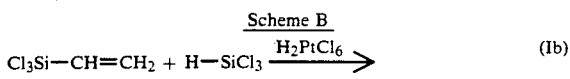

-continued

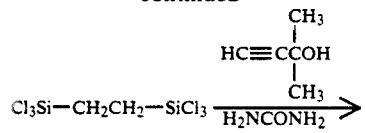

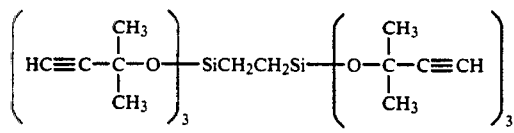

For reaction between a chlorohydrogensilane and an alkenylchlorosilane, they are preferably mixed in a molar ratio of from 2:3 to 3:2, especially in an equimolar ratio.

In general, hydrosilylation occurs in the presence of a platinum group metal addition reaction catalyst. The reaction conditions include 60° to 120° C. and 1 to 5 hours although need not be limited thereto. The platinum group metal addition reaction catalysts used herein include platinum group, palladium group and rhodium group catalysts, with the platinum group catalysts being preferred. Examples of the platinum group catalysts include platinum black, solid platinum on alumina, silica or similar supports, chloroplatinic acid, alcohol modified chloroplatinic acid, chloroplatinic acid olefin complexes, and platinum vinylsiloxane complexes. The platinum group metal addition reaction catalysts may be used in a catalytic amount, preferably 0.1 to 500 ppm, especially 2 to 200 ppm of platinum group metal based on the total weight of chlorosilane and alkenylchlorosilane.

Hydrosilylation may be effected simply by adding dropwise a chlorohydrogensilane to a reactor charged with an alkenylchlorosilane and a platinum group catalyst, for example, thereby forming a bis(chlorosilyl)ethane.

A subsequent step is dehydrochlorination between the bis(chlorosilyl)ethane and 1,1-dimethylpropargyl alcohol. Desirably, 1,1-dimethylpropargyl alcohol is added in a molar amount of 1 to 5 times, especially 1.2 to 2 times the mole of ≡Si-Cl group in the bis(chlorosilyl)ethane. This reaction is preferably carried out in the presence of an agent for promoting dehydrochlorination such as urea, which is preferably added in a molar amount of 1 to 5 times, especially 1.5 to 2.5 times the mole of ≡Si-Cl group in the bis(chlorosilyl)ethane. The preferred reaction conditions include 50° to 70° C. and 3 to 6 hours with optional adjustment.

Dehydrochlorination may be effected simply by adding dropwise a bis(chlorosilyl)ethane to a reactor charged with 1,1-dimethylpropargyl alcohol and a promoting agent, for example, thereby forming an end alkoxysilane.

There have been described novel alkoxysilanes of formula (I) which can be prepared from two types of readily available monosilane reactants by a relatively simple synthesis process and purified by distillation. By adding a predetermined amount of the alkoxysilane to addition type curable silicone compositions as a curing reaction control agent, curing reaction can be controlled to a consistent extent corresponding to the additive amount regardless of an alkoxysilane manufacturing lot. This enables precise reproducible control on silicone composition curing. In addition, because of their extremely low vapor pressure at room temperature, the alkoxysilanes allow a working life for the curable silicone compositions. When the curable silicone compositions are subjected to vacuum debubbling prior to their use, the compositions do not alter their curing behavior. Upon heat curing at temperatures between 150° C. and 180° C., cured products do not undergo differential curing between the surface and the interior and present a good outer appearance. Therefore, the alkoxysilanes of the invention are useful as agents for controlling curing reaction of addition type curable silicone compositions or the like.

Eliminated variation in quality of the alkoxysilanes among different manufacturing lots is evident from the fact that these alkoxysilanes are monomers having a definite molecular structure and can be isolated by distillation.

EXAMPLE

Examples of the present invention are given below by way of illustration and not by way of limitation.

EXAMPLE 1

A reactor was charged with 42.3 grams (0.30 mol) of methylvinyldichlorosilane and 0.1 ml of a 2.ethylhexyl alcohol solution containing 2% chloroplatinic acid. To the reactor was added dropwise 34.5 grams (0.30 mol) of methyldichlorosilane. After the completion of addition, stirring was continued for a further one hour. After cooling, the reaction solution was distilled, obtaining 74.5 grams (yield 97%) of 1,2-bis(methyldichlorosilyl)ethane having a boiling point of 109°–110° C./30 mmHg.

Next, a reactor was charged with 126.2 grams (1.50 mol) of 1,1-dimethylpropargyl alcohol and 91.3 grams (1.52 mol) of urea and heated to 55° C. To the reactor was added dropwise 64.0 grams (0.25 mol) of 1,2-bis(methyldichloro silyl)ethane obtained in the previous step. After the completion of addition, the reaction solution was stirred for 3 hours at a temperature of 50° to 60° C., cooled, washed three times with 50 ml of saturated sodium chloride water, dried over 12 grams of anhydrous sodium sulfate, and filtered. Distillation of the filtrate gave 64.7 grams (yield 58%) of a fraction having a boiling point of 127°–130° C./3 mmHg.

This fraction was examined by infrared absorption spectrum, NMR spectrum, and elemental analysis. The results are shown below, by which the fraction was identified to be a compound of the following formula.

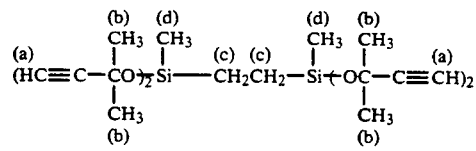

(a) to (d) are references for the description of NMR spectrum.

IR spectrum: absorption peak, cm$^{-1}$ 3310 (ethynyl H—C) 2120 (ethynyl C≡C) 1260 (methyl CH$_3$—Si) 1140 (silethylene Si—CH$_2$CH$_2$—Si)

NMR spectrum: shift, ppm (δ) (in CCl$_4$, internal standard CHCl$_3$) 2.19 (S, 2H) (a) 1.52 (S, 12H) (b) 0.93–0.82 (t, 2H) (c) −0.03 (S, 3H) (d)

Elemental analysis

|  | C | H | Si |
|---|---|---|---|
| Calcd. | 64.53 | 8.57 | 12.57 |
| Found | 64.44 | 8.25 | 12.88 |

EXAMPLE 2

As in Example 1, 53.3 grams (0.33 mol) of vinyltrichlorosilane was reacted with 46.1 grams (0.34 mol) of trichlorosilane to obtain 96.0 grams (yield 98%) of 1,2-bis(trichlorosilyl)ethane.

Next, a reactor was charged with 208.3 grams (2.48 mol) of 1,1-dimethylpropargyl alcohol and 150.2 grams (2.50 mol) of urea and heated to 55° C. To the reactor was added dropwise 81.7 grams (0.28 mol) of 1,2-bis(trichlorosilyl)-ethane obtained in the previous step. After the completion of addition, the reaction solution was stirred for 5 hours at a temperature of 50° to 60° C., cooled, washed three times with 75 ml of saturated sodium chloride water, dried over 17 grams of anhydrous sodium sulfate, and filtered. Distillation of the filtrate gave 83.4 grams (yield 52%) of a fraction having a boiling point of 107°-110° C./6'10$^{-4}$ mmHg.

This fraction was examined by infrared absorption spectrum, NMR spectrum, and elemental analysis. The results are shown below, by which the fraction was identified to be a compound of the following formula.

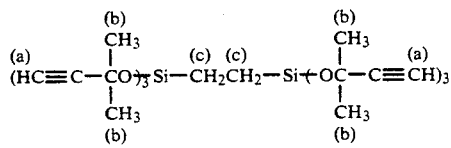

(a) to (c) are references for the description of NMR spectrum.

IR spectrum: absorption peak, cm$^{-1}$ 3300 (ethynyl H—C) 2120 (ethynyl C≡C) 1150 (silethylene Si—CH$_2$CH$_2$—Si)

NMR spectrum: shift, ppm (δ) (in CCl$_4$, internal standard CHCl$_3$) 2.26 (S, 3H) (a) 1.58 (S, 18H) (b) 0.91-0.79 (t, 2H) (c)

Elemental analysis

|  | C | H | Si |
|---|---|---|---|
| Calcd. | 65.94 | 7.95 | 9.64 |
| Found | 65.72 | 8.08 | 9.95 |

Due to their low vapor pressure, the alkoxysilanes of the present invention are effective as a curing reaction control agent for addition curing silicones. Example 3 shows the effectiveness of the alkoxysilanes as a curing control agent. In Example 3, parts are by weight, and the U procedures of mixing, deaeration and viscosity measurement are at 25° C.

EXAMPLE 3

Two mixtures were prepared by mixing 100 parts of dimethylpolysiloxane end capped with a vinyldimethylsilyl group having a viscosity of 1,000 centipoise with 8 parts of methylhydrogenpolysiloxane of the following formula:

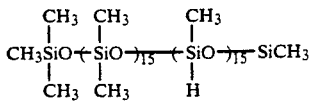

and further adding thereto 0.01 part of silane compound (a) or (b).

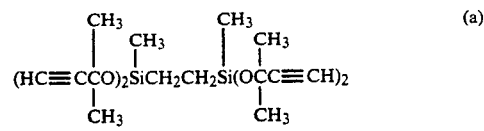

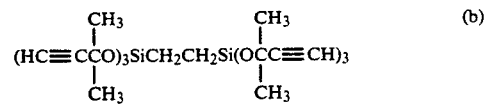

Next, compositions A and B were prepared by adding a solution of chloroplatinic acid in 2-ethylhexyl alcohol to each of the mixtures such that the platinum content was 5 ppm based on the total weight and thoroughly milling the mixture.

The compositions A and B were deaerated by allowing them to stand in a vacuum for a certain time. After deaeration, compositions A and B were allowed to stand in a constant temperature chamber at 25° C. Table 1 reports the viscosity of the compositions after 30 minutes and 6 hours from the completion of mixing.

Separately, deaerated compositions A and B were cured by heating at 150° C. Table 2 reports the time required to complete curing and the appearance of cured products.

For comparison purposes, compositions C, D, and E were prepared by the same procedure as above except that the silane compound was replaced by the following silane compounds (c), (d), and (e).

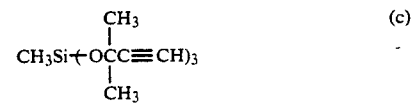

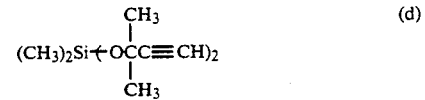

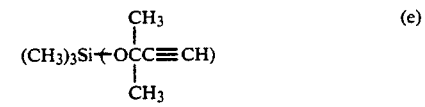

The compositions C, D, and E were deaerated in vacuum and then heat cured as in Example 1. The viscosity of the deaerated compositions and the appearance of the cured compositions are reported in Tables 1 and 2.

TABLE 1

| Deaerating condition | Time after mixing | Viscosity (centipoise at 25° C.) of compositions | | | | |
|---|---|---|---|---|---|---|
| | | A | B | C | D | E |
| 10 mm Hg/ 10 min. | 30 min. | 710 | 720 | 710 | 710 | 750 |
| | 6 hr. | 760 | 730 | 730 | 780 | cured |
| 3 mm Hg/ | 30 min. | 710 | 720 | 710 | 710 | 780 |

TABLE 1-continued

| Deaerating condition | Time after mixing | Viscosity (centipoise at 25° C.) of compositions | | | | |
|---|---|---|---|---|---|---|
| | | A | B | C | D | E |
| 20 min. | 6 hr. | 770 | 730 | 750 | 990 | cured |

TABLE 2

| De-aerating condition | Compositions | | | | |
|---|---|---|---|---|---|
| | A | B | C | D | E |
| Curing time (sec.) | | | | | |
| 10 mm Hg/ 10 min. | 45 | 70 | 70 | 45 | 10 |
| 3 mm Hg/ 20 min. | 45 | 70 | 65 | 35 | <5 |
| Appearance of cured product | | | | | |
| 10 mm Hg/ 10 min. | irregular no wrinkle | irregular no wrinkle | irregular some wrinkles | somewhat irregular many wrinkles | irregular many wrinkles |

It is evident that a curable silicone composition having an alkoxysilane blended as a curing control agent gives little change in curing behavior when the composition is deaerated in vacuum prior to use. A curable silicone composition having an alkoxysilane blended as a curing control agent can be heat cured at 150° C. into a cured product free of a defect in outer appearance which is otherwise induced by uneven curing.

Although some preferred embodiments have been described, many modifications and variations may be made thereto in the light of the above teachings. It is therefore to be understood that within the scope of the appended claims, the invention may be practiced otherwise than as specifically described.

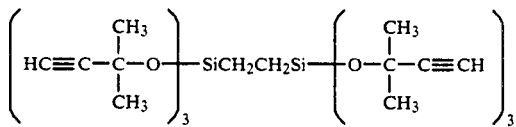

We claim:

1. An alkoxysilane of the general formula:

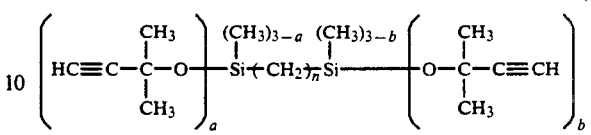

(I)

wherein letter a is equal to 2 or 3, b is equal to 0, 1, 2 or 3, and n is an integer of from 2 to 10.

2. The alkoxysilane of claim 1 which is of the following formula.

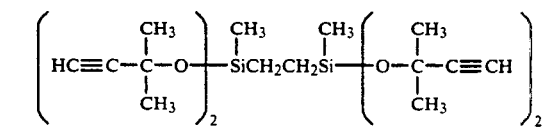

3. The alkoxysilane of claim 1 which is of the following formula.